United States Patent
Furihata et al.

(10) Patent No.: US 9,556,401 B2
(45) Date of Patent: *Jan. 31, 2017

(54) METHOD FOR PRODUCING EPA-ENRICHED OIL AND DHA-ENRICHED OIL

(75) Inventors: Kiyomi Furihata, Hachioji (JP);
Hiroyuki Kawahara, Hachioji (JP);
Hideaki Yamaguchi, Hachioji (JP);
Hideo Ikemoto, Hachioji (JP);
Nobushige Doisaki, Hachioji (JP)

(73) Assignee: NIPPON SUISAN KAISHA, LTD., Tokyo (JP)

( * ) Notice: Subject to any disclaimer, the term of this patent is extended or adjusted under 35 U.S.C. 154(b) by 78 days.

This patent is subject to a terminal disclaimer.

(21) Appl. No.: 12/669,803

(22) PCT Filed: Jul. 29, 2008

(86) PCT No.: PCT/JP2008/063550
§ 371 (c)(1),
(2), (4) Date: Jan. 20, 2010

(87) PCT Pub. No.: WO2009/017102
PCT Pub. Date: Feb. 5, 2009

(65) Prior Publication Data
US 2010/0190220 A1    Jul. 29, 2010

(30) Foreign Application Priority Data
Jul. 30, 2007 (JP) .................................. 2007-197253

(51) Int. Cl.
*C12P 7/64* (2006.01)
*C11C 1/04* (2006.01)
*C11C 3/10* (2006.01)

(52) U.S. Cl.
CPC ................. *C11C 1/045* (2013.01); *C11C 3/10* (2013.01); *C12P 7/6472* (2013.01)

(58) Field of Classification Search
None
See application file for complete search history.

(56) References Cited

U.S. PATENT DOCUMENTS

| 5,945,318 A | 8/1999 | Breivik et al. |
| 5,968,792 A * | 10/1999 | Wenzel et al. ................ 435/134 |
| 7,491,522 B2 | 2/2009 | Haraldsson et al. |
| 2006/0148047 A1 | 7/2006 | Haraldsson et al. |
| 2009/0176284 A1 | 7/2009 | Furihata et al. |

FOREIGN PATENT DOCUMENTS

| JP | 58-165796 A | 9/1983 |
| JP | 61-15692 A | 1/1986 |
| JP | 3-108489 A | 5/1991 |
| JP | 8-116982 A | 5/1996 |
| JP | 9-510091 A | 10/1997 |
| JP | 2004-285182 A | 10/2004 |
| JP | 2006-506483 A | 2/2006 |
| WO | 0073254 A1 | 12/2000 |
| WO | 2007/119811 A1 | 10/2007 |

OTHER PUBLICATIONS

J.S. Dordick, "Enzymatic catalysis in monophasic organic solvents," Enzyme Microb. Technol., Apr. 11, 1989, 194-211.
International Search Report for PCT/JP2008/063550 mailed Oct. 7, 2008.
Li Zuyi and Ward O.P., Lipase-catalyzed alcoholysis to concentrate the n-3 polyunsaturated fatty acid of cod liver oil, Enzyme and Microbial technology., 1993, vol. 15, No. 7, pp. 601-606.
Shen, Zhiping and Wijesundera, Chakra, Evaluation of Ethanolysis with Immobilized Candida antarctica Lipase for Regiospecific Analysis of Triacylglycerols Containing Highly Unsaturated Fatty Acids, Journal of the American Oil Chemist Society, vol. 83, No. 11, pp. 923-927.
Extended European Search Report corresponding to Application No. 08791785.2-1357/2172558, PCT/JP2008/063550; Date of Mailing: Apr. 24, 2015.

* cited by examiner

*Primary Examiner* — Nashaat Nashed
(74) *Attorney, Agent, or Firm* — Cantor Colburn, LLP

(57) ABSTRACT

Alcoholysis of oils and fats containing EPA and DHA is performed by a lipase having substrate specificity for fatty acids having 18 carbons or less and in the presence of a reaction additive such as magnesium oxide; then the glyceride fraction is separated; alcoholysis of the glyceride fraction is performed by a lipase having substrate specificity for fatty acids having 20 carbons or less and in the presence of a reaction additive such as magnesium oxide; and EPA-enriched oil and DHA-enriched oil are simultaneously obtained.

7 Claims, No Drawings

METHOD FOR PRODUCING EPA-ENRICHED OIL AND DHA-ENRICHED OIL

This is a U.S. national stage application of International Application No. PCT/JP2008/063550, filed on 29 Jul. 2008. Priority under 35 U.S.C. §119(a) and 35 U.S.C. §365(b) is claimed from Japanese Application No. JP2007-197253, filed 30 Jul. 2007, the disclosure of which is also incorporated herein by reference.

TECHNICAL FIELD

The present invention relates to a method for producing enriched oils containing high concentrations of eicosapentaenoic acid (EPA hereafter) and docosahexaenoic acid (DHA hereafter) respectively using a lipase reaction.

BACKGROUND ART

Eicosapentaenoic acid (EPA hereafter) and docosahexaenoic acid (DHA hereafter) are n-3 polyunsaturated fatty acids (PUFA hereafter) having a variety of biological effects, and are used as medical products, health food products, food product materials, and the like. EPA ethyl ester is used as a therapeutic agent for arteriosclerosis and hyperlipidemia, and beverages to which fish oil containing EPA and DHA has been added have been approved as a food for specified health uses. Furthermore, the demand for these fatty acids as a supplement is very high in Japan and other countries.

PUFAs have many double bonds and are therefore very unstable to oxidation. Consequently, that an enzyme reaction that proceeds under mild conditions at room temperature is very desirable for the steps involved in producing PUFA-containing oils.

There are lipase products for industrial use that are obtained from primarily microorganisms and that have the property of hardly reacting with PUFAs. PUFA-enriched oils and fats can be produced using lipases having such a property by emphasizing liberation and removal of fatty acids having few carbons. For instance, a method is disclosed whereby DHA-enriched oils and fats are produced by hydrolysis of tuna oil using *Candida cylindoracea* lipase and then removal of the free fatty acids (Patent Reference 1).

It is known that water has an important effect on enzyme activation for enzyme reactions in an organic solvent (non-Patent Reference 1). It is reported that when a PUFA is concentrated from cod lever oil using alcoholysis, which is a reaction wherein the fatty acids are severed from glycerides by exposure to an alcohol, the addition of water promotes the lipase reaction (Non-Patent Reference 2). On the other hand, it is disclosed that alcoholysis of oils and fats proceeds under virtually anhydrous conditions with certain lipases. Nevertheless, the amount of lipase used must be very high at 10% the amount of oil, and the lipase must be immobilized in order to improve productivity (Patent Reference 2).

A method is cited in Patent Reference 3 wherein an alkali salt is used when oils and fats containing long-chain polyunsaturated fatty acids as constituent fatty acids are hydrolyzed by a lipase having positions 1 and 3 specificity.

Patent Reference 1 JP (Publication of Unexamined Patent) 58-165796
Patent Reference 2 JP (National Publication) 9-510091
Patent Reference 3 JP (Publication of Unexamined Patent) 3-108489
Non-Patent Reference 1 J. S. Dordick, "Enzymatic catalysis in monophasic organic solvents," *Enzyme Microb. Technol.*, 1989, 11, Apr., 194-211.

Non-Patent Reference 2 L. Zui and O. P Ward, "Lipase-catalyzed alcoholysis to concentrate the n-3 polyunsaturated fatty acids of cod liver oil," *Enzyme Microb. Technol.*, 1993, 15, Jul., 601-606.

DISCLOSURE OF THE INVENTION

Problems to be Solved by the Invention

Although the market already carries oil that has been enriched with PUFA from fish oil and the like using lipase having the above-mentioned property, there are limits to the degree of concentration, and it is either difficult to obtain a highly concentrated product or a large amount of enzyme is necessary. An object of the present invention is to provide a method for efficiently enriching both the EPA and DHA respectively from PUFAs contained in starting oils.

Means for Solving the Problems

As a result of conducting comprehensive research of reactions using industrial lipases, the inventors discovered that the lipase reaction efficiency can be dramatically improved, even when a small amount of lipase is used, by adding a small amount of a compound selected from, for instance, magnesium oxide (MgO hereafter), magnesium hydroxide, calcium oxide, and calcium hydroxide. They further discovered that this reaction has sufficient substrate specificity and that it is appropriate for methods whereby both the EPA and DHA are highly concentrated respectively.

The present invention is primarily a production method characterized by reacting a lipase, having substrate specificity for fatty acids having 18 carbons or less, with oils and fats containing EPA and DHA as constituent fatty acids in the presence of at least one selected from the group consisting of magnesium oxide, magnesium hydroxide, calcium oxide, and calcium hydroxide as a reaction additive; severing the fatty acids having 18 carbons or less from the glyceride and then separating the glyceride fraction; and further reacting this glyceride fraction with a lipase having substrate specificity for fatty acids having 20 carbons or less in the presence of at least one compound selected from the group consisting of magnesium oxide, magnesium hydroxide, calcium oxide, and calcium hydroxide to simultaneously obtain EPA-enriched oil (as a lower alcohol ester) and DHA-enriched oil (as a glyceride fraction).

That is, the present invention is a method for producing EPA-enriched oil and DHA-enriched oil from oils and fats containing EPA and DHA as constituent fatty acids, this method comprising a) a step wherein the oils and fats are subjected to alcoholysis, or alcoholysis accompanied by hydrolysis, by a lipase having substrate specificity for fatty acids having 18 carbons or less and in the presence of an alcohol or hydrated alcohol and at least one compound selected from the group consisting of magnesium oxide, magnesium hydroxide, calcium oxide, and calcium hydroxide as a reaction additive, and an eicosapentaenoic acid and docosahexaenoic acid-enriched glyceride fraction is obtained from the resulting reaction mixture and b) a step wherein the glyceride fraction is subjected to alcoholysis, or alcoholysis accompanied by hydrolysis, by a lipase having substrate specificity for fatty acids having 20 carbons or less and in the presence of an alcohol or hydrated alcohol and at least one compound selected from the group consisting of magnesium oxide, magnesium hydroxide, calcium oxide, or calcium hydroxide as a reaction additive, and the EPA-enriched ester fraction and DHA-enriched glyceride fraction are separated from the resulting reaction mixture.

Advantages of the Invention

The present invention increases enzyme reactivity and realizes a reaction that is highly substrate specific in each step by adding a small amount of an inexpensive reaction additive such as magnesium oxide. As a result, EPA-enriched oil and DHA-enriched oil can be produced simultaneously at a high yield and inexpensively.

EMBODIMENT OF THE INVENTION

There are no special restrictions to the oils and fats used as starting materials in the present invention as long as they are oils containing EPA and DHA as fatty acids formed by the glycerides contained in these oils and fats, and examples are marine product oils including fish oil, microorganism oils, seaweed oils, and vegetable oils. When used as the starting material of the present invention, these can be dude oils (expressed oils), or they can be oils that have been subjected to some type of purification process. It is preferred that the starting materials used in the present invention have as high an EPA and DHA content as possible, and preferred lipids are sardine oil (for instance, 17% EPA and 12% DHA), tuna oil (for instance, 7% EPA and 25% DHA), bonito oil (for instance, 5% EPA and 24% DHA), and salmon oil (for instance, 9% EPA and 14% DHA).

The term "oils and fats" usually means the triglycerides of fatty acids, but in the present invention the term also includes other glycerides that lipases will affect, such as diglycerides, monoglycerides, and the like. The term "glyceride" in the present invention is a general term for the triglycerides, diglycerides, and monoglycerides of fatty acids.

The phrase "EPA or DHA-enriched" in the present invention means that the [amount of EPA or DHA/total amount of fatty acids] after the reaction is greater than the [amount of EPA or DHA/total amount of fatty acids] in the starting oils and fats, and oil having a higher [amount of EPA or DHA/total amount of fatty acids] when compared to the starting oils and fats is EPA-enriched oil or DHA-enriched oil.

The term "alcohol" in the present invention includes one or multiple types of alcohols.

The lipase reaction performed by the method of the present invention is alcoholysis wherein a fatty acid ester is produced from a glyceride. This lipase reaction is performed in a mixed solvent of alcohol and water, and can also be a reaction by which free fatty acids and fatty acid esters are produced. Examples of lower alcohol solvents used in the present invention are ethanol, methanol, 2-propanol, and butanol. Ethanol is particularly preferred.

There are no special restrictions to the lipase used in step a) of the present invention as long as it has substrate specificity to fatty acids having 18 carbons or less. Examples of preferred lipases are lipase obtained from microorganisms belonging to *Alcaligenes* sp. (Lipase QLM, Lipase QLC, Lipase QLG, Lipase PL, all produced by Meito Sangyo Co., Ltd.). Lipase QLM is particularly preferred. Lipase QLC, which is easily obtained from Meito Sangyo Co., Ltd., has the following characteristics and properties. Description: Beige powder; Activity: Approximately 60,000 U/g; Molecular weight: 31 kDa; Isoelectric point: 4.9; Optimal pH: 7 to 9; and Optimal Temperature: 65 to 70° C. Moreover, lipase QLC is lipase QLM that has been immobilized on diatomaceous earth, and lipase QLG is lipase QLM that has been immobilized on granulated diatomaceous earth.

Although there are no special restrictions to the amount of lipase used, it is preferred that the amount of lipase in powder form in terms of oils and fats be 10 units/g or more, preferably 30 units/g or more taking into consideration practicality based on the reaction rate, and it is preferred that the amount of immobilized lipase in terms of oils and fats be 0.01% (w/w) or more.

There are no special restrictions to the lipase used in step b) of the present invention as long as it has substrate specificity for fatty acids having 20 carbons or less. An example of a preferred lipase is lipase obtained from microorganisms belonging to *Thermomyces lanuginosus* (Lipozyme TL IM made by Novozymes). Lipozyme TL IM, which can be obtained from Novozymes, has the following characteristics and properties. Molecular weight: 30 kDa; Isoelectric Point: 4.8, pH: 6 to 11, Optimal Temperature: 60 to 70° C.; Immobilization Carrier: Silica Gel; Grain Size: 300 to 1,000 μm (primarily 500 to 900 μm): and Specific Gravity: 0.54 g/mL. Although there are no special restrictions to the amount of lipase used, it is preferred that the amount of lipase in powder form in terms of glyceride fraction be 10 units/g or more, preferably 30 units/g or more taking into consideration practicality based on the reaction rate, and it is preferred that the amount of immobilized lipase in terms of oils and fats be 0.01% (w/w) or more.

Magnesium oxide, magnesium hydroxide, calcium oxide, and calcium hydroxide can be used as reaction additives, but magnesium oxide is particularly preferred because it has the most effective and can be used in food products. Additives in powder, particle, or granule form are easy to handle, and those sold for industrial use can be used. There are no particular restrictions to the amount of reaction additive added, but in step a) the reaction additive is used within a range of 0.01% (w/w) to 30% (w/w), more preferably a range of 0.05% (w/w) to 5% (w/w), in terms of starting oils and fats. Moreover, in step b) the reaction additives are used within a range of 0.01% (w/w) to 30% (w/w), preferably 0.05% (w/w) to 5% (w/w), in terms of glyceride fraction of the starting materials.

There are no special restrictions to the reaction method as long as a predetermined amount of starting oils and fats, reaction additives, alcohol, and the like can be mixed. The reaction can be performed in accordance with conventional technological knowledge regarding reactions that use ordinary lipases. Generally, the reactants are stirred such that they are thoroughly mixed for a reaction time of 1 to 24 hours at a reaction temperature at which the enzyme is very active (for instance, 20 to 60°). It is also possible to use immobilized enzyme packed in a column and the like in the reaction.

When the lipase reaction is an alcoholysis reaction, after the reaction it is possible to remove the reaction additive, enzyme, and the like by, for instance, filtration or washing with an aqueous solution.

Although there are no special restrictions to the method used to separate the glyceride fraction in steps a) and b), distillation, such as molecular distillation or short-path distillation, and separation methods that use various types of chromatography can be used. The purification method can be one that is normally used for purification of oils and fats, and various types of chromatography and steam distillation are examples.

As one of the embodiment of the present invention, the lipase reaction can be performed by adding a small amount of water to the reaction system during either of steps a) and b) or both of steps a) and b). When water is added, it is added in the amount of 1% (v/v) to 30% (v/v), further preferably 5% (v/v) to 20% (v/v), in terms of the amount of lower alcohol used. The amount of water contained in the oils and fats should be taken into consideration.

The amount of lower alcohol is, for instance, 0.2 to 5 equivalents, more preferably 0.2 to 1.5 equivalents, in terms of fatty acids contained in the oils and fats or glyceride fraction in the reaction system.

The fatty acid lower alcohol esters and free fatty acids produced when step a) is performed in the presence of a hydrated lower alcohol can be removed by distillation (such as thin film distillation, molecular distillation, or short-path distillation), a deacidification step using an alkali, and the like.

The present invention is described below in specific terms using working examples, but the present invention is in no way limited to these working examples. It should be noted that the EPA and DHA content of the starting oil and glyceride fraction was determined from the gas chromatography area ratio after methyl esterification. Moreover, methyl esterification that was performed prior to gas chromatography analysis was conducted in accordance with the standard oils and fats testing method specified by the Japan Oil Chemists' Society (Japan Oil Chemists' Society Standard Methods for the Analysis of Fats, Oils and Related Materials (I), 1996, 2.4.1 Fatty acid Derivation Methods: 2.4.1.2-1996 Methyl esterification methods (boron trifluoride-methanol method)).

Working Example 1

(1) Lipase Reaction of Step a)

1.49 g of Lipase QLM (100 units/g), 20.7 g of water, 30 g (2.5% in terms of oil) of magnesium oxide (Junsei Chemical Co., Ltd., special grade reagent having a purity of 99% or higher, powder), and 207 mL of ethanol were added to 1.20 kg of purified sardine oil (17.4% EPA, 11.9% DHA, Nippon Suisan Kaisha, Ltd.) and the mixture was stirred for 16 hours at 40° C. After the reaction, the solid content was filtered and rinsed with 560 mL of 20% sulfuric acid and 200 mL of brine. Then the water content and ethanol remaining in the oil layer were distilled off to obtain 1.21 kg of oil. A small amount of the resulting oil was sampled, the glyceride fraction was separated by preparative TLC and methyl esterified, and the fatty acid composition was analyzed by gas chromatography. The analysis conditions are described below (unless otherwise noted, analysis by preparative TLC and gas chromatography was performed by the same method later).

TLC Fractionation and Methyl Esterification Conditions:

1 mL of hexane and 10 mL of saturated brine were added to 50 µL, of reaction solution and hexane extraction was performed. 150 µL, of the resulting hexane layer were applied to preparative TLC and developed using hexane:diethyl ether:acetic acid (70:30:1, volume ratio). After development, the glyceride fraction other than the ethyl ester was collected and, without further treatment of the fraction, methyl esterification was performed by methylation. In essence, 2 mL of a 1 N sodium methoxide/methanol solution were added and heated for one minute at 80° C. Then 2 mL of 1 N hydrochloric acid were added and the product was heated for one minute at 80° C. in order to stop the reaction. Next, 0.5 mL of hexane and 6 mL of saturated brine were added, the mixture was shaken and then set aside, and the hexane layer was analyzed by gas chromatography.

Gas Chromatography Conditions:
Capillary column: DB-WAX (J & W Scientific), Fused Silica Capillary Column, 0.25 mm I.D.×30 m, 0.25 µm film thickness
Carrier gas: helium
Detector: 250° C., FID
Injector: 250° C., split ratio: 100:1
Column temperature: 180° C.→3° C./min→230° C. (15 min)
Device: Hewlett Packard 6890

Moreover, after spotting a 5 wt % hexane solution (1 µL) on a silica gel rod, the rod was developed with hexane:diethyl ether:acetic acid (90:10:1, volume ratio) and the lipid composition was analyzed using TLC/FID. Tables 1 and 2 show the lipid composition and fatty acid composition of the starting sardine oil, the lipid composition (area %) of the resulting oil, and fatty acid composition (area %) of the glyceride fraction. The EPA and DHA were concentrated to 46.7% and 20.6%, respectively, in the glyceride fraction by this reaction. The yield of EPA and DHA was a high at 106.6% and 68.7%, respectively. The EPA and DHA yield (%) was calculated from the (ratio (%) of EPA (or DHA) in the glyceride fraction after the reaction×the glyceride content (%))/(ratio (%) of EPA (or DHA) in the oils and fats prior to the reaction).

TABLE 1

Fatty acid composition (area %)

| | Purified sardine oil | After step a) reaction (glyceride fraction) |
|---|---|---|
| C14:0 | 6.3 | 2.3 |
| C15:0 | 0.5 | 0.0 |
| C16:0 | 14.9 | 2.8 |
| C16:1 | 8.1 | 2.4 |
| C16:2 | 1.6 | 1.7 |
| C16:3 | 1.3 | 0.4 |
| C16:4 | 1.8 | 0.4 |
| C18:0 | 3.5 | 0.7 |
| C18:1 | 13.4 | 4.5 |
| C18:2n-6 | 1.2 | 0.3 |
| C18:3n-3 | 0.7 | 0.0 |
| C18:4n-3 | 2.5 | 0.5 |
| C20:1 | 3.1 | 2.3 |
| C20:4n-6 | 1.6 | 3.6 |
| C20:4n-3 | 0.9 | 0.3 |
| C20:5 (EPA) | 17.4 | 46.7 |
| C22:1 | 1.9 | 1.5 |
| C22:4 | 0.7 | 0.9 |
| C22:5n-3 | 2.4 | 5.8 |
| C22:6 (DHA) | 11.9 | 20.6 |
| Others | 4.6 | 2.2 |

TABLE 2

Lipid composition (area %)

| | | Purified sardine oil | After step a) reaction |
|---|---|---|---|
| | Ethyl ester | 0.0 | 43.5 |
| Glyceride fraction | Triglycerides | 100.0 | 0.0 |
| | Diglycerides | 0.0 | 9.1 |
| | Monoglycerides | 0.0 | 30.6 |
| | Free fatty acids | 0.0 | 16.9 |

(2) Glyceride Fraction Separation

The ethyl ester and fatty acids were distilled off from the oils obtained in Working Example 1 using a thin layer distillation device. The thin layer distillation device was short-path distillation device KDL-5 (evaporation area of 0.048 m²) made by UIC GmbH, and 2-pass treatment was performed at 130° C., 1×10⁻³ mbar, and 0.60 L/h. Tables 3 and 4 show the fatty acid composition (area %) and the lipid composition (area %) of the residual oil after distillation. It was confirmed that the ethyl ester and free fatty acids had been distilled off from the lipid composition and that EPA- and DHA-enriched glyceride fraction had been obtained.

TABLE 3

Fatty acid composition (area %)

|  | After thin layer distillation (after two passes) |
|---|---|
| C14:0 | 1.9 |
| C15:0 | 0.0 |
| C16:0 | 2.8 |
| C16:1 | 2.9 |
| C16:2 | 1.5 |
| C16:3 | 0.5 |
| C16:4 | 0.4 |
| C18:0 | 0.9 |
| C18:1 | 4.8 |
| C18:2n-6 | 0.3 |
| C18:3n-3 | 0.0 |
| C18:4n-3 | 0.6 |
| C20:1 | 2.4 |
| C20:4n-6 | 3.9 |
| C20:4n-3 | 0.4 |
| C20:5 (EPA) | 45.1 |
| C22:1 | 1.7 |
| C22:4 | 0.7 |
| C22:5n-3 | 5.8 |
| C22:6 (DHA) | 20.5 |
| Others | 2.7 |

TABLE 4

Lipid composition (area %)

|  | After thin layer distillation | |
|---|---|---|
|  | After 1 pass | After 2 passes |
| Ethyl ester | 4.5 | 0.8 |
| Triglycerides | 0.0 | 0.0 |
| Diglycerides | 35.2 | 44.2 |
| Monoglycerides | 54.5 | 51.7 |
| Free fatty acids | 5.8 | 3.3 |

(3) Step b) Lipase Reaction and Product Fractions

10 μL of water, 20 mg of Lipozyme TL IM (2.0% in terms of oil), 25 mg of magnesium oxide (2.5% in terms of oil), and 173 μL at of ethanol were added to 1 g of the oil (glyceride fraction) obtained in step b), and the mixture was stirred for 16 hours at 40° C. Then the solid was filtered and washed with brine, and the lipid composition of the resulting oil was analyzed. The ethyl ester and glyceride fraction were separated by preparative TLC and the fatty acid composition was analyzed. The conditions for preparative TLC were the same as those for step a) of Working Example 1 and this time analysis was performed on both the ethyl ester and the glyceride fraction. Tables 5 and 6 show the fatty acid composition (area %) and the lipid composition after the reaction. The DHA was concentrated in the glyceride fraction to 76.4% and the EPA was concentrated in the ethyl ester fraction to 52.1%, and DHA-enriched oil and EPA-enriched oil could be simultaneously obtained. The DHA yield from the glyceride fraction by this reaction was 71.6% and the EPA yield from the ethyl ester fraction was 74.9%. The DHA yield (%) was calculated from the (ratio (%) of DHA in the glyceride fraction after the reaction×the glyceride content (%) after the reaction)/(the ratio (%) of DHA in the glyceride fraction before the reaction), and the EPA yield was calculated from (the ratio (%) of EPA from the ethyl ester after the reaction×the ethyl ester content (%) after the reaction)/(the ratio (%) of EPA before the reaction).

TABLE 5

Fatty acid composition (area %)

|  | After step b) reaction | |
|---|---|---|
|  | Glyceride fraction | Ethyl ester fraction |
| C14:0 | 1.1 | 1.7 |
| C15:0 | 0.0 | 0.0 |
| C16:0 | 0.8 | 2.3 |
| C16:1 | 0.6 | 1.9 |
| C16:2 | 3.3 | 0.8 |
| C16:3 | 0.3 | 0.4 |
| C16:4 | 0.5 | 0.5 |
| C18:0 | 0.0 | 0.6 |
| C18:1 | 0.6 | 4.0 |
| C18:2n-6 | 0.0 | 0.0 |
| C18:3n-3 | 0.0 | 0.0 |
| C18:4n-3 | 0.8 | 0.7 |
| C20:1 | 0.0 | 1.9 |
| C20:4n-6 | 0.7 | 3.8 |
| C20:4n-3 | 0.0 | 0.5 |
| C20:5 (EPA) | 10.2 | 52.1 |
| C22:1 | 0.0 | 1.5 |
| C22:4 | 2.7 | 0.6 |
| C22:5n-3 | 1.2 | 7.1 |
| C22:6 (DHA) | 76.4 | 16.4 |
| Others | 0.9 | 3.1 |

TABLE 6

Lipid composition (area %)

|  | After step b) reaction |
|---|---|
| Ethyl ester | 64.8 |
| Triglycerides | 0.0 |
| Diglycerides | 1.8 |
| Monoglycerides | 17.4 |
| Free fatty acids | 15.2 |

Working Example 2

The amount of Lipozyme TL IM in step (3) of Working Example 1 was changed to 5 mg (0.5% in terms of oil) and the reaction was performed under exactly the same conditions as in step (3) of Working Example 1. Tables 7 and 8 show the results. DHA-enriched oil and EPA-enriched oil were simultaneously obtained, even when the amount of lipase was reduced. The DHA yield of the glyceride fraction in the reaction was 114.7% and the EPA yield in the ethyl ester fraction was 58.9%. (Yield results exceeding 100% are due to the fact that this yield calculation method was simplified method. That is, the FID measurement used to calculate yield is high for fatty acids having a high molecular weight, such as DHA, because relative sensitivity increases with an increase in molecular weight. The same is true for the following working examples.)

TABLE 7

| | Fatty acid composition (area %) | |
|---|---|---|
| | After step b) reaction | |
| | Glyceride fraction | Ethyl ester fraction |
| C14:0 | 1.2 | 2.4 |
| C15:0 | 0.0 | 0.0 |
| C16:0 | 0.7 | 3.5 |
| C16:1 | 0.6 | 2.5 |
| C16:2 | 2.0 | 1.0 |
| C16:3 | 0.6 | 0.3 |
| C16:4 | 0.9 | 0.9 |
| C18:0 | 0.0 | 5.1 |
| C18:1 | 0.6 | 0.3 |
| C18:2n-6 | 0.0 | 0.0 |
| C18:3n-3 | 0.0 | 0.0 |
| C18:4n-3 | 1.3 | 0.4 |
| C20:1 | 0.0 | 1.8 |
| C20:4n-6 | 1.8 | 4.0 |
| C20:4n-3 | 0.4 | 0.6 |
| C20:5 (EPA) | 24.8 | 54.8 |
| C22:1 | 0.0 | 1.9 |
| C22:4 | 2.1 | 0.5 |
| C22:5n-3 | 2.0 | 8.3 |
| C22:6 (DHA) | 58.8 | 7.2 |
| Others | 2.4 | 4.6 |

TABLE 8

| Lipid composition (area %) | |
|---|---|
| | After step b) reaction |
| Ethyl ester | 48.5 |
| Triglycerides | 0.0 |
| Diglycerides | 6.5 |
| Monoglycerides | 33.5 |
| Free fatty acids | 10.2 |

Working Example 3

DHA-enriched oil and EPA-enriched oil were prepared using winterized and purified EPA rich sardine oil (29.0% EPA, 12.5% DHA, Nippon Suisan Kaisha, Ltd.) as the starting lipid. The step a) reaction involved using 1.2 kg of purified sardine oil, 1.49 g of Lipase QLM, 20.7 mL of water, 60 g of magnesium oxide, and 207 mL of ethanol, reacting the mixture for 16 hours at 40° C., and performing the same treatment as in Working Example 1. Then 2-pass thin layer distillation was performed under the same conditions as in Working Example 1 to obtain a glyceride fraction. The step b) reaction involved using 1 g of the oil obtained from step a), 10 μL of water, 20 mg of Lipozyme TL IM, 25 mg of magnesium oxide, and 173 μL of ethanol, and reacting the mixture for 16 hours at 40° C. The ethyl ester and glyceride fractions were both fractionated by preparative TLC (the conditions were the same as in Working Example 1). Table 9 shows the fatty acid composition of starting purified sardine oil, after step a) reaction mixture, residual oil after 2-pass thin layer distillation, and fractions after step b) reaction. Table 10 shows the lipid composition after the step a) and step b) reactions. It was possible to simultaneously obtain high concentrations by a two-step reaction, with the EPA concentration being 73.9% and the DHA concentration being 50.8%. In the step a) reaction the EPA yield was 95.8% and the DHA yield was 53.7%, and in the step b) reaction the EPA yield of the ethyl ester fraction was 62.6% and the DHA yield of the glyceride fraction was 114.6%.

TABLE 9

| | Fatty acid composition (area %) | | | | |
|---|---|---|---|---|---|
| | Winterized and purified EPA rich sardine oil | After step a) reaction (glyceride fraction) | After thin layer distillation (after 2 passes) | After step b) reaction | |
| | | | | Glyceride fraction | Ethyl ester fraction |
| C14:0 | 5.3 | 1.1 | 0.7 | 1.3 | 0.7 |
| C15:0 | 0.0 | 0.0 | 0.1 | 0.0 | 0.0 |
| C16:0 | 7.5 | 0.8 | 0.7 | 0.7 | 0.8 |
| C16:1 | 8.6 | 1.4 | 1.3 | 0.8 | 1.1 |
| C16:2 | 1.9 | 1.1 | 0.9 | 1.6 | 0.5 |
| C16:3 | 2.3 | 0.4 | 0.3 | 0.6 | 0.5 |
| C16:4 | 4.0 | 0.5 | 0.5 | 1.1 | 0.0 |
| C18:0 | 1.9 | 0.0 | 0.1 | 0.0 | 1.6 |
| C18:1 | 8.7 | 1.6 | 1.5 | 0.5 | 0.0 |
| C18:2n-6 | 1.1 | 0.0 | 0.2 | 0.0 | 0.0 |
| C18:3n-3 | 0.9 | 0.0 | 0.1 | 0.0 | 0.0 |
| C18:4n-3 | 4.4 | 0.5 | 0.6 | 1.4 | 0.6 |
| C20:1 | 0.9 | 0.3 | 0.3 | 0.0 | 0.3 |
| C20:4n-6 | 1.6 | 3.7 | 3.5 | 1.8 | 4.1 |
| C20:4n-3 | 1.3 | 0.3 | 0.3 | 0.3 | 0.4 |
| C20:5 (EPA) | 29.0 | 65.4 | 62.0 | 33.4 | 73.9 |
| C22:1 | 0.0 | 0.0 | 0.7 | 0.0 | 0.0 |
| C22:4 | 2.1 | 0.5 | 0.2 | 1.4 | 0.3 |
| C22:5n-3 | 3.0 | 5.5 | 5.4 | 2.0 | 6.9 |
| C22:6 (DHA) | 12.5 | 15.8 | 14.8 | 50.8 | 7.6 |
| Others | 3.1 | 1.3 | 5.7 | 2.4 | 1.0 |

TABLE 10

| | After step a) reaction | After step b) reaction |
|---|---|---|
| Lipid composition (area %) | | |
| Ethyl ester | 36.2 | 52.5 |
| Triglycerides | 0.0 | 0.0 |
| Diglycerides | 6.8 | 3.0 |
| Monoglycerides | 35.7 | 30.4 |
| Free fatty acids | 22.3 | 14.1 |

Conditions for executing the present invention were studied as shown below in Reference Examples 1 through 13

Reference Example 1

1.65 mg of Lipase QLM (*Alcaligenes* sp., Meito Sangyo Co., Ltd) (100 units/g), 17 μL of water, MgO (Junsei Chemical Co., Ltd., special grade reagent, purity of 99% or higher) (0.25% (w/w) or 2.5% (w/w) in terms of oil), and 170 μL it of ethanol (0.75 equivalents in terms of fatty acids) were added to 1 g of purified sardine oil (28.2% of EPA, 12.5% of DHA, Nippon Suisan Kaisha, Ltd.), and stirred for 16 hours at 40° C. After the reaction, the solid content was filtered and the filtrate was extracted with hexane. The glyceride fraction was separated by preparative TLC using the following method.

The resulting glyceride fraction was methyl esterified and the fatty acid composition was analyzed by gas chromatography. The conditions for preparative TLC, methyl esterification, and gas chromatography analysis were the same as in Working Example 1.

3.3 mg of Lipase PS (*Burkholderias cepacia*, Amano Enzymes) (100 units/g) were reacted under the same conditions.

By way of comparison, ethanolysis with the each lipase was performed under the same above-mentioned conditions with the exception that no water or MgO was added, only water was added, or only MgO was added at 0.25% (w/w).

The lipid composition of the glyceride fraction was analyzed using TLC/FID (Iatroscan TH-10, Mitsubishi Kagaku Yatron Corporation) by spotting a 5 wt % hexane solution (1 μL) on a silica gel rod and then developing the rod using hexane:diethyl ether:acetic acid (90:10:1, volume ratio). The glyceride and ester peak area ratios were obtained from the resulting charts, and the glyceride yield was calculated based on these ratios. The EPA and DHA yields were calculated from (the PUFA ratio (%) of the glyceride after reaction×the glyceride content (%))/(the PUFA ratio (%) before the reaction). Table 11 shows the results of the EPA and DHA area %, the EPA and DHA fatty acid yield, and glyceride yield. Table 12 shows the results of the comparative examples.

When the results in Table 11 are compared with the comparative example results in Table 12, it is clear that the addition of water and MgO has an effect on EPA and DHA concentration even with the same amount of lipase. Moreover, it is clear that the EPA and DHA become more concentrated as the amount of MgO added increases. Furthermore, the EPA and DHA yields are very high and fatty acid selectivity of this reaction is maintained.

TABLE 11

| | Starting purified sardine oil | Lipase QLM 0.25% MgO + water | Lipase QLM 2.5% MgO + water | Lipase PS 0.25% MgO + water | Lipase PS 2.5% MgO + water |
|---|---|---|---|---|---|
| EPA area % | 28.8 | 50.6 | 61.5 | 52.2 | 59.7 |
| DHA area % | 12.5 | 16.3 | 16.2 | 15.6 | 17.9 |
| EPA yield (%) | | 98.5 | 97.5 | 93.2 | 91.7 |
| DHA yield (%) | | 90.4 | 91.7 | 83.6 | 70.2 |
| Glyceride yield (%) | | 67.8 | 50.6 | 60.5 | 49.1 |

TABLE 12

| | Lipase QLM | Lipase QLM + water | Lipase QLM + MgO | Lipase PS | Lipase PS + water | Lipase PS + MgO |
|---|---|---|---|---|---|---|
| EPA area % | 36.1 | 43.0 | 41.7 | 30.7 | 45.0 | 30.1 |
| DHA area % | 15.2 | 17.5 | 16.4 | 12.9 | 17.1 | 12.3 |
| EPA yield (%) | 99.5 | 94.8 | 98.5 | 99.6 | 85.9 | 99.6 |
| DHA yield (%) | 99.2 | 89.0 | 90.0 | 98.6 | 75.2 | 97.5 |
| Glyceride yield (%) | 83.4 | 74.6 | 69.8 | 96.2 | 55.0 | 98.0 |

Reference Example 2

Using as the starting material sardine oil (15.7% EPA, 8.99% DHA, Nippon Suisan Kaisha, Ltd.) having lower EPA and DHA contents than the sardine oil used in Reference Example 1, ethanolysis was performed for 16 hours at 40° C. under the same conditions as in Reference Example 1 after adding 1.65 mg of Lipase QLM (100 units/g), 17 μL of water, 2.5% (w/w) MgO, and 170 μL of ethanol to 1 g of oils and fats. Table 13 shows the area % and yield of EPA and DHA and glyceride yield.

TABLE 13

| | Lipase QLM 2.5% MgO + water |
|---|---|
| EPA area % | 43.5 |
| DHA area % | 17.3 |
| EPA yield (%) | 95.5 |
| DHA yield (%) | 80.5 |
| Glyceride yield (%) | 41.9 |

Reference Example 3

2 mg of Lipozyme TL IM (*Thermomyces lanuginosus*, Novozymes) (0.1% (w/w) in terms of oil), 34 µL of water, MgO (0.25% (w/w) or 2.5% (w/w)), and 340 µL of ethanol were added to 2 g of purified tuna oil (6.75% of EPA, 24.3% of DHA, Nippon Suisan Kaisha, Ltd.), and the mixture was stirred for 16 hours at 40° C. By way of comparison, ethanolysis was performed under the same above-mentioned conditions with the exception that no water or MgO was added, only water was added, or 0.25% (w/w) of MgO only was added. After the reaction, the solid content was filtered, the glyceride fraction was separated by preparative TLC, methyl esterification was performed, and the fatty acid composition was analyzed. Table 14 shows the EPA and DHA fatty acids yield and glyceride yield, and Table 15 shows the EPA and DHA area %, fatty acid yield, and glyceride yield of the comparative example.

When Lipozyme TL IM was used, the degree of concentration of the DHA concentration increased and ethanolysis of the EPA proceeded. The degree of enrichment of the DHA concentration improved with an increase in the amount of MgO added. Even though the same amount of enzyme was used in the comparative example, the DHA was hardly concentrated.

TABLE 14

|  | Purified tuna oil | Lipozyme TL IM 0.25% MgO + water | Lipozyme TL IM 2.5% MgO + water |
|---|---|---|---|
| EPA area % | 6.8 | 9.4 | 8.4 |
| DHA area % | 24.3 | 48.2 | 68.7 |
| EPA yield (%) |  | 69.6 | 37.0 |
| DHA yield (%) |  | 99.1 | 83.5 |
| Glyceride yield (%) |  | 50.0 | 29.6 |

TABLE 15

|  | Lipozyme TL IM | Lipozyme TL IM + water | Lipozyme TL IM + MgO |
|---|---|---|---|
| EPA area % | 7.2 | 7.2 | 7.1 |
| DHA area % | 26.2 | 26.5 | 25.5 |
| EPA yield (%) | 99.2 | 99.0 | 99.5 |
| DHA yield (%) | 99.6 | 99.8 | 99.5 |
| Glyceride yield (%) | 97.2 | 93.5 | 98.0 |

Reference Example 4

In order to investigate the effects of reaction additives other than MgO, nine reaction additives were added at 1% (w/w) in terms of starting oil and reacted under the same reaction conditions as in Reference Example 1. That is, 1.65 mg of Lipase QLM (*Alcaligenes* sp., Meito Sangyo Co., Ltd) (100 units/g), 17 µL of water, the nine types of reaction additives shown in Table 16 at 1% (w/w) in terms of oil, and 170 µL of ethanol (0.75 equivalents in terms of fatty acids) were added to 1 g of purified sardine oil (28.2% EPA, 12.5% DHA, Nippon Suisan Kaisha, Ltd.), and the mixture was stirred for 16 hours at 40° C. Once the reaction was over, the solid content was filtered, the glyceride fraction was separated by preparative TLC, methyl esterification was performed, and the fatty acid composition was determined. Table 16 shows the EPA area % of the glyceride fraction. It is clear that in addition to MgO, magnesium hydroxide, calcium oxide, and calcium hydroxide have an EPA-enriching effect.

TABLE 16

|  | EPA area % | Manufacturer | Grade | Purity min % |
|---|---|---|---|---|
| Magnesium oxide | 56.3 | Junsei Chemical Co., Ltd. | Special grade | 99 |
| Magnesium hydroxide | 54.5 | Wako Pure Chemical Industries, Ltd. | First grade | 97 |
| Magnesium carbonate (basic) | 44.7 | Nacalai Tesque, Inc. | Special grade | MgCO$_3$ 60 to 55% MgO 40 to 45% |
| Magnesium chloride | 30.7 | Wako Pure Chemical Industries, Ltd. | Special grade | 98 |
| Calcium oxide | 46.9 | Wako Pure Chemical Industries, Ltd. | Special grade | 99.9 |
| Calcium hydroxide | 46.6 | Nacalai Tesque Inc. | Special grade | 95 |
| Calcium chloride | 29.6 | Nacalai Tesque Inc. | Special grade | 98.5 |
| Calcium nitrate | 30.1 | Nacalai Tesque Inc. | Special grade | 99.5 |
| Sodium carbonate | 29.9 | Wako Pure Chemical Industries, Ltd. | Special grade | 99.5 |
| Potassium bicarbonate | 36.2 | Nacalai Tesque, Inc. | Special grade | 99.7 |

Reference Example 5

Production of EPA-Enriched Oils and Fats by Lipase QLM 0.83 g of Lipase QLM (*Alcaligenes* sp, Meito Sangyo Co., Ltd.), 17 g of water, 2.5 g of MgO, and 173 mL of ethanol were added to 1 kg of purified sardine oil (28.2% EPA, 12.5% DHA, Nippon Suisan Kaisha, Ltd.), and the mixture was stirred for 16 hours at 40° C. After centrifugation, the solid content was removed, the ethanol was distilled off, and 1.06 kg were obtained. The product was washed with dilute sulfuric acid, rinsed with warm water, the ester and fatty acids were distilled off using a thin layer distillation device, and 583 g of EPA-enriched oil were obtained as the glyceride fraction. The fatty acid composition was measured to be 48.3% of EPA and 17.3% of DHA.

Reference Example 6

Production of DHA-Enriched Oils and Fats by Lipozyme TL IM 1 g of Lipozyme TL IM (*Thermomyces lanuginosus*, Novozymes), 17 g of water, 5 g of MgO, and 173 mL of ethanol were added to 1 g of purified tuna oil (6.75% EPA and 24.3% DHA) and stirred for 16 hours at 40° C. After filtering the solid content, the ethanol was distilled off and 1.07 kg were obtained. After rinsing with phosphoric acid, the product was rinsed with warm water, the ester and fatty acids were distilled off by a molecular distillation device, and 416 g of DHA-enriched oil were obtained as glyceride fraction. The fatty acid composition was measured to be 9.4% of EPA and 52.8% of DHA.

Reference Example 7

Study of the Amount of MgO Added

Alcoholysis was performed under the same conditions as in Reference Example 1, that is, 1.65 mg of Lipase QLM (100 units/g), 17 µL of water, MgO (0 to 10% (w/w) in terms of oil)), and 170 µL of ethanol (0.75 equivalent in terms of fatty acids) were added to 1 g of purified sardine oil (28.2% EPA and 12.5% DHA, Nippon Suisan Kaisha, Ltd.) and the mixture was stirred for 16 hours at 40° C.

Table 17 shows the results. The reaction was promoted and the EPA was concentrated in proportion to an increase in the amount of MgO added.

TABLE 17

| Amount of MgO added | EPA area % | DHA area % |
|---|---|---|
| 0 | 43.6 | 17.1 |
| 0.05% | 46.7 | 16.1 |
| 0.1% | 47.2 | 16.2 |
| 0.25% | 50.6 | 16.3 |
| 1% | 56.3 | 17.0 |
| 2.5% | 61.5 | 16.2 |
| 5% | 66.8 | 15.1 |
| 10% | 67.6 | 15.4 |

Reference Example 8

Study of Amount of Ethanol 0.83 mg of Lipase QLM (50 units/g), 17 µL of water, MgO (0.25% (w/w) in terms of oil), and ethanol at 0.5 to 1.5 equivalents in terms of fatty acids were added to 1 g of purified sardine oil (28.2% EPA, 12.5% DHA, Nippon Suisan Kaisha, Ltd.) and alcoholysis was performed by stirring for 16 hours at 40° C.

Table 18 shows the results. It is clear that the preferred amount of ethanol is 0.5 to 1.5 equivalents in terms of fatty acids.

TABLE 18

| | Ethanol (equivalents in terms of fatty acids) | | | | |
|---|---|---|---|---|---|
| | 0.5 | 0.67 | 0.75 | 1 | 1.5 |
| EPA area % | 43.1 | 46.38 | 46.3 | 46.5 | 40.2 |
| DHA area % | 16.7 | 15.77 | 17.0 | 17.4 | 16.3 |

Reference Example 9

Study of Amount of Lipase Used 10 to 50 units/g of Lipase QLM, 17 µL of water, MgO (0.25 to 1% (w/w) in terms of oil), and 0.75 equivalent of ethanol in terms of fatty acids were added to 1 g of purified sardine oil (28.2% EPA, 12.5% DHA, Nippon Suisan Kaisha, Ltd.), and alcoholysis was performed by stirring for 16 hours at 40° C.

Table 19 shows the results. It is clear that the preferred amount of lipase is 25 units/g or more. Moreover, it was confirmed that, even with the same amount of lipase, by increasing the amount of MgO the reactivity could be increased.

TABLE 19

| QLM (units/g) | 10 | 25 | 30 | 50 | 50 |
|---|---|---|---|---|---|
| MgO (%) | 2.5 | 2.5 | 1 | 0.25 | 2.5 |
| EPA area % | 32.1 | 37.17 | 48.2 | 47.8 | 63.9 |
| DHA area % | 13.1 | 15.4 | 17.2 | 17.2 | 17.2 |
| EPA yield (%) | 98.99 | 99.2 | 98.4 | 98.5 | 96.5 |

Reference Example 10

Study of Reaction Time 1.65 mg of Lipase QLM (100 units/g), 17 µL of water, MgO (0.25% (w/w) in terms of oil), and one equivalent of ethanol in terms of fatty acids were added to 1 g of purified sardine oil (28.2% EPA, 12.5% DHA, Nippon Suisan Kaisha, Ltd.), and alcoholysis was performed by stirring for 0 to 24 hours at 40° C.

Table 20 shows the results.

TABLE 20

| Reaction time | 0 | 1 | 2 | 4 | 6 | 7 | 16 | 24 |
|---|---|---|---|---|---|---|---|---|
| EPA area % | 28.8 | 39.6 | 42.7 | 44.0 | 44.5 | 46.8 | 50.6 | 53.4 |
| DHA area % | 12.0 | 15.8 | 15.6 | 16.4 | 15.7 | 17.0 | 16.3 | 16.0 |

Comparative Example

Lipase Reaction in which MgO and Water were not Used

Lipase QLM (100 to 1,000 units/g) and ethanol (one equivalent in terms of fatty acids) were added to 1 g of purified sardine oil (28.2% EPA, 12.5% DHA, Nippon Suisan Kaisha, Ltd.) and alcoholysis was performed by stirring for 16 hours at 40° C.

TABLE 21

| QLM (units/g) | 100 | 250 | 500 | 750 | 1,000 |
|---|---|---|---|---|---|
| EPA area % | 36.1 | 41.4 | 45.9 | 46.7 | 46.3 |
| DHA area % | 15.2 | 36.1 | 16.2 | 17.92 | 17.97 |
| EPA yield (%) | 85.1 | 76.1 | 69.1 | 72.2 | 71.6 |

Reference Example 11

Application to Coho Salmon Extracted Oil 2.0 mg (0.2%) of Lipozyme TL IM (*Thermomyces lanuginosus*, Novozymes), 10 µL of water, MgO (Junsei Chemical Co., Ltd., special grade, purity of 99% or higher) (0.5% (w/w) or 2.5% (w/w) in terms of oil), and 170 µL of ethanol (0.75 equivalent in terms of fatty acids) were added to 1 g of Coho salmon extracted oil (9.8% EPA, 14.0% DHA), and the mixture was stirred for 16 hours at 40° C. After the reaction, the solid content was filtered, the glyceride fraction was separated by preparative TLC, methyl esterification was performed, and the fatty acid composition was analyzed by gas chromatography. The same conditions as in Working Example 1 were used for preparative TLC, methyl esterification, and gas chromatography analysis.

Moreover, by way of comparison, ethanolysis was performed under the above-mentioned conditions with the exception that no water or MgO was added.

Table 22 shows the results of the glyceride fraction EPA and DHA area %, the EPA and DHA fatty acid yield, and the glyceride yield. Table 23 shows the results of the comparative example.

TABLE 22

|  | Starting Coho salmon extracted oil | 0.2% Lipozyme TL IM 0.5% MgO + Water | 0.2% Lipozyme TL IM 2.5% MgO + Water |
|---|---|---|---|
| EPA area % | 9.8 | 14.0 | 14.0 |
| DHA area % | 14.0 | 30.7 | 45.3 |
| EPA + DHA area % | 23.8 | 44.7 | 59.3 |
| EPA yield (%) |  | 69.6 | 29.1 |
| DHA yield (%) |  | 107.0 | 66.3 |
| Glyceride yield (%) |  | 48.8 | 20.5 |

TABLE 23

|  | 0.2% Lipozyme TL IM Without MgO nor water |
|---|---|
| EPA area % | 10.33 |
| DHA area % | 15.15 |
| EPA + DHA area % | 25.48 |
| EPA yield (%) | 98.9 |
| DHA yield (%) | 96.9 |
| Glyceride yield (%) | 95.28 |

Reference Example 12

Application to Pollack Extracted Oil 1.65 mg of Lipase QLM (100 units/g), 17 µL of water, 2.5% (w/w) MgO, and 170 µL of ethanol were added to 1 g of Pollack extracted oil (12.3% EPA, 7.9% DHA) as the starting oils and fats and ethanolysis was performed for 16 hours at 40° C. Moreover, similarly, water and MgO were added with 5 mg (0.5%) of Lipozyme TL IM and ethanolysis was performed. Table 24 shows the results of the area % and yield of EPA and DHA and glyceride yield. When Lipase QLM was used EPA was concentrated, and when Lipozyme TL IM was used DHA was concentrated. The EPA and DHA were concentrated such that their combined area % was at least twice that of the starting material.

By way of comparison, Table 25 shows the results of performing ethanolysis under the above-mentioned conditions with the exception that no MgO or water was added.

TABLE 24

|  | Starting pollack extracted oil | Lipase QLM 100 units/g 2.5% MgO + Water | 0.5% Lipozyme TL IM 2.5% MgO + Water |
|---|---|---|---|
| EPA area % | 12.3 | 30.9 | 14.0 |
| DHA area % | 7.9 | 12.9 | 38.3 |
| EPA + DHA area % | 20.2 | 43.8 | 49.4 |
| EPA yield (%) |  | 103.7 | 18.3 |
| DHA yield (%) |  | 73.7 | 78.1 |
| Glyceride yield (%) |  | 45.1 | 16.2 |

TABLE 25

|  | Lipase QLM 100 units/g Without MgO nor water | 0.5% Lipozyme TL IM Without MgO nor water |
|---|---|---|
| EPA area % | 15.8 | 18.6 |
| DHA area % | 9.9 | 16.0 |
| EPA + DHA area % | 25.7 | 34.5 |
| EPA yield (%) | 101.0 | 64.3 |
| DHA yield (%) | 97.8 | 64.1 |
| Glyceride yield (%) | 78.6 | 79.4 |

Reference Example 13

Application to Sunfish Liver Oil 1.65 mg of Lipase QLM (100 units/g), 17 µL of water, 2.5% (w/w) MgO, and 170 µL of ethanol were added to 1 g of Sunfish liver oil (5.1% arachidonic acid (AA), 4.2% EPA, 7.7% docosapentaenoic acid (DPA), and 10.5% DHA) as the starting oils and fats, and ethanolysis was performed for 16 hours at 40° C. Moreover, similarly, water and MgO were added with 5 mg of Lipozyme TL IM (0.5%) and ethanolysis was performed. Table 26 shows the area % and yield of AA, EPA, DPA, and DHA and glyceride yield. In contrast to the fact that AA, EPA, DPA and DHA were concentrated when Lipase QLM was used, only DHA was concentrated when Lipozyme TL IM was used.

By way of comparison, Table 27 shows the results of performing ethanolysis under the above-mentioned conditions with the exception that no MgO or water was added.

TABLE 26

|  | Starting sunfish liver oil | Lipase QLM 100 units/g 2.5% MgO + Water | 0.5% Lipozyme TL IM 2.5% MgO + Water |
|---|---|---|---|
| AA area % | 5.1 | 12.9 | 2.8 |
| EPA area % | 4.2 | 10.7 | 2.6 |
| DPA area % | 7.7 | 17.9 | 3.6 |
| DHA area % | 10.5 | 17.5 | 59.8 |
| AA + EPA + DPA + DHA area % | 27.6 | 59.0 | 68.8 |
| AA yield (%) |  | 95.7 | 8.6 |
| EPA yield (%) |  | 96.8 | 9.9 |
| DPA yield (%) |  | 98.0 | 7.5 |
| DHA yield (%) |  | 81.1 | 90.5 |
| Glyceride yield (%) |  | 44.8 | 15.9 |

TABLE 27

|  | Lipase QLM 100 units/g Without MgO nor water | 0.5% Lipozyme TL IM Without MgO nor water |
|---|---|---|
| AA area % | 6.5 | 5.6 |
| EPA area % | 5.3 | 4.5 |
| DPA area % | 10.4 | 8.7 |
| DHA area % | 13.5 | 12.8 |
| AA + EPA + DPA + DHA area % | 35.7 | 31.7 |
| AA yield (%) | 98.5 | 90.3 |
| EPA yield (%) | 99.1 | 89.2 |
| DPA yield (%) | 104.9 | 93.1 |
| DHA yield (%) | 100.1 | 100.0 |
| Glyceride yield (%) | 67.9 | 82.3 |

The invention claimed is:
1. A method for producing eicosapentaenoic acid-enriched oil and docosahexaenoic acid-enriched oil from oils and fats containing eicosapentaenoic acid and docosahexaenoic acid as constituent fatty acids, said method comprising:
   a) a step wherein said oils and fats are subjected to alcoholysis accompanied by hydrolysis, by a lipase having substrate specificity for fatty acids having 18 carbons or less and in the presence of an aqueous alcohol and magnesium oxide as a reaction additive, and an eicosapentaenoic acid and docosahexaenoic acid-enriched glyceride fraction is obtained from the resulting reaction mixture, wherein water is added in the amount of 5% (v/v) to 20% (v/v) in terms of amount of the aqueous alcohol, and b) a step wherein said glyceride fraction is subjected to alcoholysis accompanied by hydrolysis, by a lipase having substrate specificity for fatty acids having 20 carbons or less and in the presence of an aqueous alcohol and magnesium oxide as a reaction additive, and the eicosapentaenoic acid-enriched ester fraction and docosahexaenoic acid-enriched glyceride fraction are separated from the resulting reaction mixture, wherein water is added in the amount of 5% (v/v) to 20% (v/v) in terms of amount of the aqueous alcohol;

wherein the lipase used in step a) is a lipase obtained from a microorganism belonging to *Alcaligenes* sp. and the lipase used in step b) is a lipase obtained from a microorganism belonging to *Thermomyces lanuginosus*;

and wherein the oils and fats used in step a) are fish oil.

2. The method according to claim 1, wherein the lipase used in step a) is Lipase QLM®.

3. The method according to claim 1, wherein the lipase used in step b) is Lipozyme TL IM®.

4. The method according to claim 1, wherein the amount of reaction additive added in step a) and/or step b) is 0.01 to 30% (w/w) in terms of oils and fats.

5. The method according to claim 1, wherein the alcohol is a lower alcohol selected from the group consisting of ethanol, methanol, 2-propanol, and butanol.

6. The method according to claim 1, wherein in step (a) water is added in the amount of 10% (v/v) to 20% (v/v) in terms of amount of the aqueous alcohol.

7. The method according to claim 1, wherein in step (b) water is added in the amount of 5.78% (v/v) to 20% (v/v) in terms of amount of the aqueous alcohol.

* * * * *